United States Patent [19]

Mazany

[11] Patent Number: 5,585,510

[45] Date of Patent: Dec. 17, 1996

[54] LIGATED POLYOXOMETALATES AND METHODS FOR THEIR SYNTHESIS

[75] Inventor: Anthony M. Mazany, Akron, Ohio

[73] Assignee: The B. F. Goodrich Company, Akron, Ohio

[21] Appl. No.: 265,610

[22] Filed: Jun. 24, 1994

[51] Int. Cl.$^6$ .................................. C07F 11/00; C07F 9/02
[52] U.S. Cl. .................................................. 556/20; 556/57
[58] Field of Search .......................................... 556/20, 57

[56] References Cited

PUBLICATIONS

Sethuraman et al., J. Am. Chem. Soc., vol. 103, pp. 7666–7667, (1981).

Primary Examiner—Porfirio Nazario-Gonzalez
Attorney, Agent, or Firm—Thoburn T. Dunlap

[57] ABSTRACT

Polyoxometalates are provided which are highly soluble in organic solvents, including monomer mixtures utilized in reaction injection molding. High solubility is obtained by organic moieties incorporated in the cation and anion of compounds having the formula $[R^1{}_m ER^2{}_{m'}]_n M_x O_y L_z$. These compounds provide improved solubility while maintaining catalyst activity within reaction injection molding formulations. A method is also provided for preparing these polyoxometalates within an aqueous acidic medium, wherein ligands are incorporated in the complex simultaneously with the formation of the polyoxometalate complex.

20 Claims, No Drawings

LIGATED POLYOXOMETALATES AND METHODS FOR THEIR SYNTHESIS

FIELD OF THE INVENTION

The present invention relates to polynuclear metal oxides or polyoxometalates, such as polymolybdates and polytungstates, which are highly soluble in organic solvents. More particularly, the present invention relates to ligated polyoxometalates and methods for their production.

BACKGROUND OF THE INVENTION

The term "polyoxometalates", as used herein, is a collective term which includes isopolymolybdates, isopolytungstates, and heteropoly species. Certain organoammonium polyoxometalates have found use as catalyst precursors for the ring-opening metathesis polymerization of dicyclopentadiene (DCPD) and other monomers having norbornene structures. U.S. Pat. No. 4,380,617 to Minchak et al. and U.S. Pat. No. 4,426,502 to Minchak describe the use of organoammonium molybdates and tungstates in polymerizing norbornene-type monomers by ring-opening polymerization. These precursors comprise an organoammonium cation in combination with a molybdate or tungstate anion. The disclosed catalysts provide high monomer conversion (greater than 99 percent) when utilized in bulk polymerization processes such as reaction injection molding (RIM). The catalyst will sustain high exotherms, which helps to provide high monomer conversion. The RIM process employs two components: an A component which contains an aluminum alkyl cocatalyst and a B component which contains the organoammonium molybdate or tungstate catalyst component. A significant advance of the disclosed catalyst components over traditional catalysts (WCl$_6$ and MoCl$_5$) is that it is less reactive to air and water, and it is less likely to induce prepolymerization of the monomer. These catalyst components are also more soluble in organic solvents, such as the DCPD reactive monomer employed in RIM systems, than traditional catalyst components.

The organoammonium cations derived from the tertiary amines of these precursors, such as tridodecylamine, are good at solubilizing molybdate anions in organic media. However, the large size of some of the anions limits the solubility of the catalyst component in organic media. For example, some of the catalyst components are only slightly soluble in hexane. Improvements are desired to extend the shelf-life of RIM system formulations.

Initial reports of organopolyoxometalates date back to 1908. Syntheses for the organoammonium molybdates are described in U.S. Pat. No. 4,406,840 to Kroenke, which describes tri(tridecyl)ammonium molybdate; U.S. Pat. No. 4,406,839 to Kroenke et al., which describes a process for preparing amine molybdates in a two-phase system; U.S. Pat. No. 4,406,838 to Kroenke, which describes trioctylammonium molybdates; and U.S. Pat. No. 4,406,837 to Kroenke, which describes methyltri(capryl)ammonium molybdates. These amine molybdates are produced by reacting an amine with a molybdate compound in the presence of an acidic aqueous medium. The synthesis of amine molybdates in the presence of an acid salt is described by Kroenke in U.S. Pat. No. 4,217,292. The basic synthesis of organophosphorus and organoarsenic pentamolybdate anions of ligated polyoxometalates, is described by Kwak et al., *J. Am. Chem. Soc.* (1975) 97, 5735, and Kwak et al., *Inorg. Chem.* (1976) 15, 9776. Other ligated polymolybdates and polytungstates are described by Liu et al., *J. Chem. Ed.* (1990), Vol. 67, No. 10. However, these ligated polyoxometalates are not known to be soluble in hydrocarbons.

SUMMARY OF THE INVENTION

It is an object of the present invention to provide polyoxometalates which are highly soluble in organic solvents such as cyclohexane.

It is another object of the present invention to provide polyoxometalate complexes which are more soluble in reaction injection molding (RIM) formulations than the organoammonium molybdate and tungstate compounds.

It is another object of the present invention to provide ligated polyoxometalates with organo-substituted onium cations such as ammonium, phosphonium, arsonium, or sulfonium groups.

It is a further object of the present invention to provide a method for producing ligated polyoxometalates having organo-substituted cationic groups within an aqueous medium.

Another object of the present invention is to provide bulk polymerizable storage stable catalyst/monomer feed formulations wherein the catalyst remains soluble in the monomer.

Another object of the invention is to provide a process for the in-mold bulk polymerization of norbornene functional monomers.

It is a further object of the present invention to provide a method for producing ligated polyoxometalates having organo-substituted cationic groups within an organic/aqueous dual-phase medium.

Upon further study of the specification and appended claims, further objects and advantages of this invention will become apparent to those skilled in the art.

These and other objects are achieved in providing the ligated polyoxometalates with organo-substituted cations of the formula:

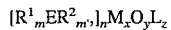

$$[R^1{}_m ER^2{}_{m'}]_n M_x O_y L_z$$

wherein: E represents nitrogen, phosphorus, arsenic, or sulfur; M represents molybdenum or tungsten; O represents oxygen; L represents a ligand selected from the group consisting of substituted-phosphonates, substituted-phosphinates, substituted-arsonates, substituted-stibonates, deprotonated hydroxycarboxylates, deprotonated hydroxydicarboxylates, deprotonated hydroxytricarboxylates, deprotonated dihydroxybenzene, and mixtures thereof; $R^1$ is independently selected from branched and unbranched $C_1$ to $C_{20}$ alkyl, $C_2$ to $C_{20}$ alkenyl, $C_5$ to $C_{20}$ cycloalkyl, $C_6$ to $C_{24}$ aryl, $C_6$ to $C_{24}$ aryloxy, $C_7$ to $C_{40}$ alkaryl, and ring structures formed with another $R^1$ group, including those wherein one or two —CH$_2$— groups are replaced by functional groups selected from —O—, —C(O)—, —OC(O)—, and —CH(OH)—; $R^2$ independently represents hydrogen, or the radicals defined under $R^1$, when E is nitrogen, $R^1$ and $R^2$ are subject to the proviso that all of the $R^1$ and $R^2$ radicals cannot be hydrogen, and the sum of carbon atoms on all of the $R^1$ and $R^2$ radicals is at least 20; and when E is arsenic, phosphorus, and sulfur the sum of all carbon atoms on all of the $R^1$ and $R^2$ radicals is at least 16; n=6x–2y–Qz, wherein x and y represent the number of M and O atoms based on the valence of +6 for molybdenum or tungsten and –2 for oxygen; Q is the charge on the ligand L; z is 1 to 6; and when E is nitrogen m=3, m'=1, when E is arsenic or phosphorus m=3, m'=1, and when E is sulfur m=2, m'=0.

When L is a substituted-phosphonate, the substituted-phosphonate is represented by the following formula:

$$R^3PO_3^{(2-)}$$

wherein:

R$^3$ represents hydrogen, hydroxy, branched or unbranched C$_1$ to C$_{20}$ alkyl, branched and unbranched C$_1$ to C$_{19}$ carboxyalkyl, or branched and unbranched hydroxyalkyl, C$_5$ to C$_{20}$ cycloalkyl, C$_2$ to C$_{20}$ alkenyl, C$_6$ to C$_{24}$ aryl, C$_6$ to C$_{24}$ aryloxy, C$_7$ to C$_{40}$ aralkyl, deprotonated polyols, C$_6$ to C$_{24}$ protonated aminoaryl, and C$_1$ to C$_{20}$ protonated aminoalkyl;

When L is a substituted-phosphinate, the substituted-phosphinate is represented by the following formula:

$$R^3PO_2H^{(-)}$$

wherein:

R$^3$ is as defined above;

When L is a deprotonated hydroxycarboxylate, the deprotonated hydroxycarboxylate is selected from substituted and unsubstituted C$_6$ to C$_{24}$ aromatic deprotonated hydroxy acids wherein the deprotonated hydroxy and carboxy groups are located on contiguous aromatic ring carbon atoms and when substituted said substituents are independently selected from branched and unbranched C$_1$ to C$_{20}$ alkyl groups, halogen groups, and mixtures thereof, and the deprotonated α-hydroxyacids are represented by the following formula:

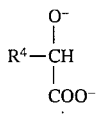

wherein:

R$^4$ represents branched and unbranched C$_1$ to C$_{20}$ alkyl;

When L is a deprotonated hydroxydicarboxylate, the deprotonated hydroxydicarboxylate is represented by the following formula:

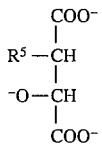

wherein

R$^5$ represents hydrogen, branched and unbranched C$_1$ to C$_{20}$ alkyl, C$_2$ to C$_{20}$ alkenyl and C$_6$ to C$_{24}$ aryl, and optionally one or two of the deprotonated oxygen atoms can be protonated;

When L is a deprotonated hydroxytricarboxylate, the deprotonated hydroxytricarboxylate is represented by the formula:

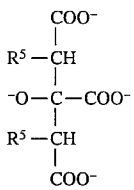

wherein

R$^5$ is independently selected from the group defined above and;

When L is deprotonated dihydroxy benzene, the deprotonated dihydroxybenzene is represented by the following formula:

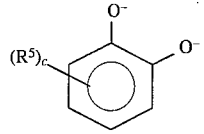

wherein

R$^5$ is independently selected from radicals as defined above, and c is 0 to 4.

In another aspect of this invention, a process is provided for producing ligated polyoxometalates with organo-substituted cationic groups which comprises reacting within an aqueous acidic medium, a polyoxometalate selected from polyoxotungstates and polyoxomolybdates; a ligand-forming compound selected from phosphorus-, antimony-, or arsenic-based organo-substituted acids, and organic compounds selected from hydroxycarboxylic acids and dihydroxy compounds, and salts thereof; and an organo-substituted cation-forming compound selected from organonitrogen, organophosphorus, organoarsenic, and organosulfides having secondary or tertiary amine phosphine, arsine, or sulfide groups or a salt thereof and quaternary ammonium, phosphonium, or arsonium salts.

DETAILED DESCRIPTION

Ligated polyoxometalates are provided with high solubility in organic solvents, such as cyclohexane, and norbornene functional monomer formulations used in in-mold bulk polymerization, e.g., RIM, such as blends based on dicyclopentadiene (DCPD). By norbornene functional is meant monomers having at least one norbornene group in the molecule. The catalyst compounds comprise polyoxometalate anions having organo-substituted ligands incorporated therein and organo-substituted onium cations to aid solubility in organic media. These compounds exhibit superior solubility to the prior octamolybdate complexes due to the relatively smaller ring structure, while maintaining the same overall charge and the same number of organo-substituted cations to aid solubility. Therefore, although the cluster size is reduced, solubilization provided by the organo-substituted cations is not lost. The incorporation of ligands into the polyoxometalate anion also allows the addition of organic moieties and heteroatoms which may influence the solubility, stability, and reactivity of the cluster. Smaller polyoxometalates frequently rearrange during synthesis, yielding a range of cluster sizes. The incorporation of ligands stabilizes the polyoxometalate structure.

The ligated polyoxometalates of this invention also exhibit excellent reactivity in in-mold bulk polymerization processes such as in RIM and RTM (reaction transfer molding) systems. Some form catalysts that can provide monomer-to-polymer conversion rates greater than 99%, as determined by thermal gravimetric analysis (TGA) at 400° C. High exotherms (160°–220° C.), which are necessary for effective RIM manufacturing procedures, are also provided.

The ligated polyoxometalates of this invention may be produced by reacting within an aqueous acidic medium, a polyoxometalate, a ligand-forming compound, and a cation-forming compound selected from organo-nitrogen, phosphorus, arsenic, or sulfur compounds or salts thereof. The reaction components are added to an aqueous medium before the addition of acid. Preferably, the cation-forming compound is not introduced until after the complete dissolution of the ligand-forming compound. The aqueous solution is preferably heated before the addition of acid to aid dissolution of the oxopolymetalate. Suitable acids include inorganic acids, such as hydrochloric acid, nitric acid, sulfuric acid, and the like or mixtures thereof. The amount of acid used may vary widely from about one-half to ten or more molar equivalents of acid per molar equivalent of polyoxometalate. However, one molar equivalent is typically preferred. The acid is preferably metered into the aqueous medium at a slow rate.

Sufficient water is included in the reaction mixture to ensure a consistency which enables it to be easily stirred. Optionally, an organic solvent may be introduced into the aqueous medium to provide a two-phase reaction medium. When utilized, the organic solvent is immiscible in water; and, preferably, the product is soluble therein. Examples include aliphatic solvents such as pentane, hexane, heptane, octane, decane, petroleum ether, and the like. Other examples include aromatic solvents, such as benzene, toluene, naphthalene, xylene, and the like; and chlorinated solvents, such as tetrachloroethane, chlorobenzene, and the like. Water-soluble organic solvents, such as the aliphatic alcohols methanol, ethanol and the like, and ketones, such as acetone, butanone, and the like, can be used if desired. Preferred solvents are selected from the group consisting of benzene, toluene, hexane, heptane, methylene chloride, and cyclohexane.

Where the reaction mixture is heated before the introduction of the inorganic acid, a temperature range of 60°–70° C. is preferred. After the acid is introduced, the reaction mixture is refluxed for about 0.25–16 hours, preferably 1–4 hours, and preferably with stirring. The duration of the reaction depends on the starting materials. After the reaction is complete, the aqueous phase is decanted off. The product collects as a syrup or precipitate at the bottom of the reactor in the absence of organic solvent. This syrup/precipitate (or organic phase) is washed with water. Where a syrup/precipitate is obtained, it is dissolved in an organic solvent (or monomer suitable for RIM formulations) after washing with water.

The organic phase or product/solvent mixture is gently heated to remove all water by azeotropic distillation. If neat product is desired, the solvent is removed, preferably by vacuum distillation. The hexane-water azeotrope boils at about 61.6° C., while hexane only boils at 69° C. The cyclohexane-water azeotrope boils at 69.8° C. The boiling point for cyclohexane alone is about 81° C. The product obtained from these reactions is readily identifiable by elemental, infrared, and NMR analysis.

Molar ratios of the starting materials (polyoxometalate, organoamine, cation-forming compound, and ligand-forming compound) do not influence the nature of the products formed as much as the identity of these starting materials. Incorporation of ligands provide stability of the products formed. Therefore, molar ratios of polyoxometalate/ligand-forming compound/cation-forming compound can range widely within the reaction medium and still provide the desired product.

The ligand-forming compound is preferably a phosphorus compound or a hydroxcarboxylic acid or salt thereof. Other suitable ligand-forming compounds provide ligands based on antimony, sulfur, arsenic and other organic compounds such as dihydroxy compounds. The most preferred ligand-forming compounds are phosphorus compounds selected from the group consisting of organo-substituted phosphonic acids, such as those of the formula $R^3P(O)(OH)_2$; diphosphonic acids, phosphinic acids, such as those of the formula $R^3P(O)(OH)H$; diphosphinic acids, and salts thereof, such as the corresponding organo-substituted sodium phosphinates and sodium phosphonates. Analogous arsonic, arsinic, stibinic, stibonic, sulfinic, and sulfonic acids, their diacids, and salts thereof can be used to profice the corresponding As, Sb, or S ligand. $R^3$ is hydrogen, hydroxy, branched or unbranched, $C_1$ to $C_{20}$ alkyl, branched or unbranched carboxyalkyl, branched or unbranched $C^1$ to $C_{20}$ hydroxyalkyl, $C_5$ to $C_{20}$ cycloalkyl, $C_2$ to $C_{20}$ alkenyl, $C_1$ to $C_{20}$ aryl, $C_6$ to $C_{24}$ aryloxy, $C_7$ to $C_{24}$ aralkyl, $C_6$ to $C_{24}$ aryl, deprotonated polyols, $C_6$ to $C_{24}$ protonated aminoaryl, and $C_1$–$C_{20}$ protonated aminoalkyl. Examples of preferred phosphorus compounds include phenyl phosphonic acid, phenyl phosphinic acid, disodium phenylphosphate, deprotonated polyols such as derived from disodium(glycerol)-2-phosphate, 2-carboxyethyl-phosphonic acid, methyl phosphonic acid, aminophenyl phosphonic acid, butyl phosphonic acid, and methylene diphosphonic acid. Analogous arsenic compounds are also preferred.

The polyoxometalates used in the process of this invention comprise the metals tungsten and molybdenum, including $Mo^{VI}$ and $Mo^V$. These compounds can vary widely in composition and structure. Sodium or ammonium salts of these compounds are typically used for the reaction, such as sodium molybdates and sodium tungstates of the formula $Na_2MO_4.2H_2O$, wherein M is molybdenum or tungsten. Suitable molybdates also include $(NH_4)_6Mo_7O_{24}.4H_2O$, $MoO_3$, and $(NH_4)_2Mo_2O_7$.

The compounds used in the process of this invention to provide the organo-substituted cations include organoamines, organophosphines, organoarsines, and organosulfides. These cation-forming compounds have secondary sulfide and/or tertiary amine, phosphine, or arsine groups and are of the formula $R^1ER^2$, wherein $R^1$ and $R^2$ are defined in detail below and E is N, As, P, or S. Salts of the amines are also suitable and typically are of the formula $R^1NH(B)$, wherein B is an anion, preferably chlorine, bromine, nitrate, or sulfate.

The organic moieties on the cation-forming compounds are critical to providing solubility of the resultant products within organic media, such as cyclohexane or hexane as used in solution polymerization or norbornene functional monomer mixtures used in RIM. The cation-forming compounds of nitrogen contain at least 20 carbon atoms to provide adequate solubility within organic media. All of the $R^1$ and $R^2$ radicals cannot be hydrogen since such a condition will render the catalyst essentially insoluble in hydrocarbons and most organic solvents. The cation-forming compounds of arsenic, phosphorus, and sulfur contain at least 16 carbon atoms to provide adequate solubility in organic media. Typically, the number of carbon atoms ranges from 20–75 for all cation forming compounds. Functional groups may be introduced to further enhance the solubility of the resultant cation within the specific organic media. Good solubility and cost effectiveness are obtained when $R^1$ is $C_8H_{17}$-$C_{18}H_{37}$ and $R^2$ is hydrogen. There is a practical limit to the size of the aliphatic groups in that as they increase in size, the percentage of molybdenum or tungsten content of the resultant product decreases. This may require an increased loading of the product formed when used as a catalyst component in RIM formulations or solution polymerization. Generally, increasing the chain length of the aliphatic hydrocarbons of R increases solubility in organic media. Preferably, each susbtituent contains 10 or more carbon atoms.

While particular attention has been given to the aliphatic radicals of $R^1$ and $R^2$, the substituents within the scope of $R^1$ and $R^2$ also include acyclic, aromatic, and heterocyclic structures, such as where $R^1$ or $R^2$ is cyclohexyl, phenyl, or two of the $R^1$ substituents form a ring structure. The substituents within the scope of $R^1$ include radicals which contain functional groups so as to make the cation more lipophilic, providing higher solubility within organic media. Such functional groups include carboxy groups, C(O)O; carbonyl groups, C(O)—; and hydroxy groups, —OH. The cation-forming compounds utilized may contain additional amine, phosphine or arsine groups, which may be primary, secondary, or tertiary in structure. In addition to tailoring the R substituents to enhance lipophilic properties, its identity may be tailored to provide greater interaction between the resultant cation and the anion.

Commercially available organoamines which are suitable for use in this process include Adogen® 381, $(C_8H_{17})_3N$; Adogen® 382, $(C_{10}H_{21})_3N$; Alamine® 304 $(C_{12}H_{25})_3N$; Adogen® 340, tri(hydrogenated tallow)amine; $(C_{18}H_{37})_{0.65}(C_{16}H_{33})_{0.35}(C_{14}H_{29})_{0.05}N$. Salts of these amines can be easily obtained and are suitable for use in this process. Other specific amines and ammonium salts which are conveniently available include di(tridecyl)amine, tri(octyl)methylammonium chloride, tri(dodecyl)ammonium nitrate, tetrapentylammonium bromide, di(dodecyl)dimethylammonium bromide, and dioctadecylammonium bromide.

The ligated polyoxometalates provided by this invention comprise an onium cation component and a ligated molybdate or tungstate anion component of the formula:

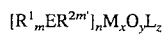
$$[R^1{}_mER^2{}_{m'}]_nM_xO_yL_z$$

The cation represented by $(R^1{}_mER^2{}_{m'})$ is taken n times, wherein n=6x−2y−Qz; x and y represent the number of M and O atoms in the anion (to be described below) based on the valence of +6 for molybdenum and tungsten and −2 for oxygen. Q is the charge on the ligand L, and z is 1 to 6. Preferably, the number value of n ranges from 2 to 6, more preferably the number value of n is 2 or 4, and most preferably the value of n is 4. A larger number of cations improves the solubility of the present compounds within organic media due to the higher number of organic moieties present. The cation is preferably an organoammonium cation (E=N) derived from an organoamine having secondary or tertiary amine groups with organic substituents, as described above. Cations based on phosphorus, arsenic, and sulfur (E=P, As, and S) can be used as well. When E is nitrogen, arsenic or phosphorus m is 3 and m' is 1, and when E is sulfur m is 2 and m' is 0.

$R^1$ is independently selected from branched and unbranched $C_1$ to $C_{20}$ alkyl, $C_2$ to $C_{20}$ alkenyl, $C_5$ to $C_{20}$ cycloalkyl, $C_6$ to $C_{24}$ aryl, $C_6$ to $C_{24}$ aryloxy, $C_7$ to $C_{40}$ alkaryl, and ring structures formed with another $R^1$ group, including those wherein one or two —CH$_2$— groups are replaced by functional groups selected from —O—, —C(O)—, —OC(O)—, and —CH(OH)—. Aliphatic substituents having 8 to 18 carbon atoms are preferred. Most preferably, each substituent has at least 10 carbon atoms. Substituents which may be used to enhance the lipophilic nature of the products may also be introduced. For example, additional amine groups or carbonyl groups, carboxyl groups, or hydroxyl groups may be present so as to enhance solubility within the organic solvent of choice.

$R^2$ is independently selected from hydrogen or $R^1$. Preferably, $R^2$ is selected from hydrogen, methyl, or aliphatic substituents having 8 to 18 carbon atoms.

When E is nitrogen, the selection of $R^1$ and $R^2$ are subject to the provisos that not more than three of $R^1$ and $R^2$ can be hydrogen, and the sum of all carbon atoms represented by $R^1$ and $R^2$ is at least 20, preferably from 20 to 75, so as to aid solubility, and when E is arsenic, phosphorus, and sulfur, the sum of all carbon atoms on all $R^1$ and $R^2$ radicals is at least 16.

The ligated molybdate and tungstate anion portion of the catalyst component is represented by $M_xO_yL_z$ wherein M is molybdenum or tungsten, and x, y, and z are as defined above. Numerically, the preferred value of x ranges from 1 to 12, more preferably 2 to 8, and the preferred value of y ranges from 2 to 46, more preferably 8 to 26. The value of z ranges from 1 to 6, preferably 1 to 4.

The ligands represented by L introduce organic functionality to the anion so as to aid solubility within organic media such as the norbornene functional monomers used in the RIM process. These ligands also confer solubility in other organic solvents such as cyclohexane and hexane utilized as organic media in solution polymerization processes.

The ligand incorporates a multivalent atom selected from phosphorus, arsenic, antimony, and sulfur. Phosphorus is preferred because of reduced toxicity. The multivalent atoms can be substituted with organic substituents which will be described below. The organic substituents are significant in that they aid in solubility within organic media. Ligand L is also selected from organic compounds such as deprotonated hydroxycarboxylic acids and deprotonated dihydroxy compounds such as deprotonated hydroxycarboxylates, deprotonated hydroxydicarboxylates, deprotonated hydroxytricarboxylates, and deprotonated dihydroxybenzene.

When the multivalent atom is phosphorus, the ligand is a substituted phosphonate $(R^3PO_2^{(2-)})$ or substituted phosphinate $(R^3PO_2H^{(-)})$ wherein $R^3$ is selected from the group consisting of hydrogen, hydroxy, branched and unbranched $C_1$ to $C_{20}$ alkyl, branched and unbranched $C_1$ to $C_{20}$ carboxyalkyl, branched and unbranched $C_1$ to $C_{20}$ hydroxyalkyl, $C_5$ to $C_{20}$ cycloalkyl, $C_2$ to $C_{20}$ alkenyl, $C_6$ to $C_{24}$ aryl, $C_6$ to $C_{24}$ aryloxy, $C_7$ to $C_{40}$ aralkyl, deprotonated polyols such as, for example, deprotonated glycerol, (e.g., protons are removed from the hydroxy groups), protonated $C_1$ to $C_{20}$ aminoalkyl and protonated $C_6$ to $C_{24}$ aminoaryl (e.g., protonated amino=—NH$_3^+$).

When the multivalent atom is arsenic, the As atom can be substituted in place of phosphorus in the forgoing formulae.

When L is a deprotonated hydroxycarboxylate, the ligand is selected from substituted and unsubstituted $C_6$ to $C_{24}$ aromatic hydroxy acids wherein the hydroxy and carboxy moieties are deprotonated and located on contiguous aromatic ring carbon atoms as exemplified by the following formulae:

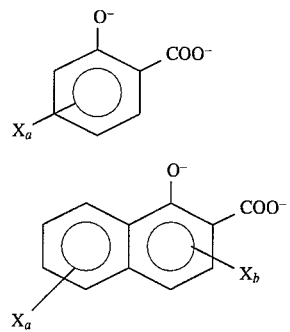

wherein X is independently selected from branched and unbranched $C_1$ to $C_{20}$ alkyl and halogen and a is 0–4 and b is 0–2. If X is present it can be taken once or can be taken any number of times about the ring structure. Again it is emphasized that the deprotonated hydroxy and carboxy groups can be located anywhere about the ring(s) so long as they are bonded to contiguous ring carbon atoms. Preferred deprotonated aromatic hydroxyacids are salicylate and substituted salicylates wherein X is methyl or bromine, and deprotonated hydroxynaphthoate derived from 1-hydroxy-2-naphthoic acid, 2-hydroxy-1-naphthoic acid or 3-hydroxy-2-naphthoic acid.

The term deprotonated hydroxyacid is also representative of deprotonated α-hydroxyacids of the following formula:

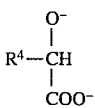

wherein $R^4$ is selected from branched and unbranched $C_1$ to $C_{20}$ alkyl, preferably $C_1$ to $C_4$ alkyl, and most preferably methyl.

The deprotonated hydroxydicarboxylates are represented by the following formula:

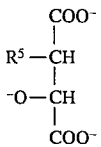

wherein $R^5$ is hydrogen, branched and unbranched $C_1$ to $C_{20}$ alkyl, $C_2$ to $C_{20}$ alkenyl, and $C_6$ to $C_{24}$ aryl. Preferably $R^5$ is hydrogen. Optionally, one or two of the deprotonated oxygen atoms in the above formula can be protonated.

The deprotonated hydroxytricarboxylates are represented by the following formula:

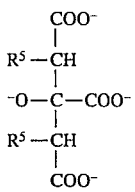

wherein $R^5$ is independently selected from radicals as previously defined.

The deprotonated dihydroxy benzene can be represented by the following formula:

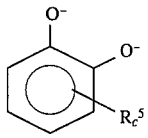

wherein $R^5$ is independently selected from radicals as previously defined, and c is 0 to 4.

Specific ligated organoammonium polyoxometalates provided by this invention include:
tetrakis[tri(dodecyl)ammonium]di(phenylphospho)pentamolybdate,
tetrakis[tri(isodecyl)ammonium]di(phenylphospho)pentamolybdate,
tetrakis[tri(isooctyl)ammonium]di(phenylphospho)pentamolybdate,
tetrakis[tri(octyl)ammonium]di(phenylphospho)pentamolybdate,
tetrakis[di(dodecyl)ammonium]di(phenylphospho)pentamolybdate,
tetrakis[tri(dodecyl)ammonium]di(phenylphospho)pentatungstate,
tetrakis[tri(dodecyl)ammonium]di(glycerophosphate)pentamolybdate,
tetrakis[tri(dodecyl)ammonium]di(ethylphospho)pentamolybdate,
tetrakis[tri(dodecyl)ammonium]di(methylphospho)pentamolybdate,
di[trikis(dodecyl)ammonium]di(aminophenylphospho)pentamolybdate,
tetrakis[tri(dodecyl)ammonium]di(butylphospho)pentamolybdate.

The norbornene functional monomers that can be polymerized by the catalysts of the present invention are characterized by the presence of at least one norbornene moiety defined structurally as follows:

Preferred species are identified by the formulae below:

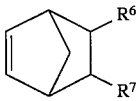

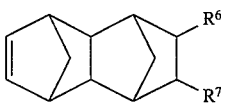

wherein $R^6$ and $R^7$ are independently selected from hydrogen, $C_1$ to $C_{20}$ alkyl, $C_2$ to $C_{20}$ alkenyl, $C_1$ to $C_{10}$ alkylidenyl, $C_6$ to $C_{24}$ aryl, and saturated and unsaturated cyclic groups containing 3 to 12 carbon atoms formed by $R^6$ and $R^7$ taken together with the ring carbon atoms bonded thereto. It will be noted by those skilled in the art that when $R^6$ or $R^7$ represents alkylidenyl the bond line between the $R^6$ and/or $R^7$ substituents and the ring carbon atom bonded thereto represents a double bond.

In accordance with this definition, suitable norbornene functional monomers include substituted and unsubstituted norbornene, dicyclopentadiene, dihydrodicyclopentadiene, symmetical and asymmetrical trimer of cyclopentadiene, oligomers of cyclopentadiene, tetracyclododecene, tetracyclododecadiene, and mixtures thereof.

Preferred substituents on the norbornene functional monomers include $C_1$ to $C_{10}$ alkyl, $C_2$ to $C_6$ alkenyl, $C_6$ to $C_{12}$ aryl and $C_1$ to $C_5$ alkylidenyl, more preferably ethylidenyl.

Preferred norbornene functional monomers include dicyclopentadiene, trimers of cyclopentadiene, methyltetracyclododecene, ethylidene norbornene (e.g., 5-ethylidenyl-2-norbornene), vinyl norbornene, 2-norbornene, and other norbornene functional monomers such as 5-methyl-2-norbornene, 5,6-dimethyl-2-norbornene, 5-ethyl-2-norbornene, 5-butyl-2-norbornene, 5-hexyl-2-norbornene, 5-octyl-2-norbornene, and 5-dodecyl-2-norbornene.

In order to obtain thermoset polymers small mounts of crosslinking monomers, e.g., symmetrical trimer of cyclopentadiene and tetracyclododecadiene can be incorporated into the monomer mixture. Other crosslinking type monomers that are useful herein are disclosed in U.S. Pat. No. 4,701,510 which is hereby incorporated by reference.

In the in-mold bulk polymerization of norbornene functional monomers, the catalyst component of the present invention and a cocatalyst component are dissolved in separate aliquots of norbornene functional monomer to form two polymerizable reactant feed solutions. Each feed composition is not reactive until mixed with the other. Reactant streams from each of the catalyst and cocatalyst reactant feed solutions are mixed to form a reactive solution which is subsequently conveyed into a mold. A chemical reaction, i.e., via ring-opening metathesis polymerization, occurs in the mold transforming the monomer into a tough, hard thermoset polymer. Optionally, when quicker cycle times are desired, the mold can be preheated before conveying the reactive monomer solution therein. The mold temperature employed is greater than room temperature, preferably above about 30° C., more preferably between about 40° to about 200° C., and most preferably between about 50° to about 120° C.

Any suitable cocatalyst can be employed so long as it reacts with the catalysts of this invention to produce a polymer product. In in-mold bulk polymerization processes the metathesis catalyst system, i.e., the catalyst and cocatalyst, should be sufficiently active to attain at least 95 percent monomer to polymer conversion. Suitable cocatalysts include organoaluminum and organoaluminum halides such as for example, alkylaluminum compounds and alkylaluminumhalides selected from monoalkylaluminum dihalides, dialkylaluminum monohalides (diethylaluminumchloride), aluminum sesquihalides and trialkylaluminum (triethylaluminum). Other alkylaluminum halides include compounds selected from alkoxyalkylaluminum halides and aryloxyalkylaluminum halides as set forth in U.S. Pat. No. 4,426,502 which is hereby incorporated by reference.

A monomer to polymer conversion enhancing agent such as silicon tetrachloride can also be added to the monomer mixture.

The polyoxometalate catalyst components of this invention, or mixtures thereof are employed at a level of 0.01 to 50 millimoles of M atoms (e.g., molybdenum or tungsten per mole of total monomer, and preferably 0.1 to 10 millimoles per mole of total monomer. The molar ratio of the cocatalyst to the catalyst component ranges from about 200:1 or more to about 1:10, preferably 50:1 to 2:1 of aluminum to the molybdenum and/or tungsten atoms. The heated mold thermally initiates onset of the polymerization reaction.

The properties of the polymer product can be modified by the addition of additives to the monomer composition. The additives can be dissolved or dispersed in at least one of the monomer reactant solutions. Suitable additives include elastomers, antioxidants, UV stabilizers, fillers, flame retardants, lubricants, fragrances, pigments, foaming agents, and the like. The invention is not limited to a two reactant stream process. A third reactant stream (or a plurality of streams) containing additional reactants or additives can be employed in the process.

Without further elaboration, it is believed that one skilled in the art can, using the preceding description, utilize the present invention to its fullest extent. The following preferred specific embodiments are, therefore, to be construed as merely illustrative and not limitative of the remainder of the disclosure in any way whatsoever.

In the foregoing and in the following examples, all temperatures are set forth uncorrected in degrees Celsius; and, unless otherwise indicated, all parts and percentages are by weight.

The entire disclosures of all applications, patents, and publications, cited above and below, are hereby incorporated by reference.

EXAMPLES

Syntheses of Ligated Polyoxometalates

Example 1

Sodium molybdate, $Na_2MoO_4 \cdot 2H_2O$ (25.0 g), was dissolved in deionized water (50.0 g), and phenylphosphonic acid, $C_6H_5P(O)(OH)_2$ (6.53 g), was also dissolved in deionized water (50.0 g). The two solutions were combined in a 500 mL round-bottom flask fitted with a water-cooled condenser and heating mantle. Tridodecylammonium nitrate (48.34 g) was then added. The mixture was warmed and dilute hydrochloric acid (16.0 g concentrated HCl plus 100.0 g deionized water) was added slowly to the phosphonic acid/molybdate/amine salt solution with stirring. The mixture was heated to reflux, with stirring, for 2 hours and then allowed to cool to room temperature. A dark green syrup collected at the bottom of the flask, and the aqueous phase was decanted from the syrup and discarded. The syrup was rinsed twice with deionized water, cyclohexane (250.0 g) was added, and the reactor was fitted with a Dean-Stark trap. The solution was heated to reflux and continued until all water had been removed by azeotropic distillation. The remaining solvent was removed by vacuum distillation. The syrup obtained was readily soluble in hexane and dicyclopentadiene, and the infrared spectrum was consistent with the structure $[(C_{12}H_{25})_3NH]_4\{(C_6H_5P)_2Mo_5O_{21}\}$.

Example 2

Sodium molybdate, $Na_2MoO_4 \cdot 2H_2O$ (100.0 g), was dissolved in deionized water (400.0 g), and phenylphosphonic acid, $C_6H_5P(O)(OH)_2$ (26.12 g), was also dissolved in deionized water (100.0 g). The two solutions were combined in a 2 L round-bottom flask fitted with a water-cooled condenser and heating mantle. Tridodecylammonium nitrate (193.4 g) was then added. The mixture was warmed and dilute sulfuric acid (25.33 g concentrated $H_2SO_4$ plus 50.0 g deionized water) was added slowly to the phosphonic acid/molybdate/amine salt solution with stirring. The mixture was heated to reflux, with stirring, for 90 minutes and then allowed to cool to room temperature. A dark green syrup collected at the bottom of the flask, and the aqueous phase was decanted from the syrup and discarded. The syrup was rinsed twice with deionized water, hexane (250.0 g) was added, and the reactor was fitted with a Dean-Stark trap. The solution was heated to reflux and continued until all water had been removed by azeotropic distillation. The remaining solvent was removed by vacuum distillation. The dark green syrup obtained was readily soluble in hexane and dicyclopentadiene, and the infrared spectrum was consistent with the structure $[(C_{12}H_{25})_3NH]_4\{(C_6H_5P)_2Mo_5O_{21}\}$.

Example 3

The procedure of Example 2 was essentially followed utilizing the amine, tri(i-decyl)amine.

Sodium molybdate, $Na_2MoO_4 \cdot 2H_2O$ (100.0 g), was dissolved in deionized water (450.0 g), and phenylphosphonic acid, $C_6H_5P(O)(OH)_2$ (26.12 g), was also dissolved in deionized water (75 g). The two solutions were combined in a 2 L round-bottom flask fitted with a water-cooled condenser and heating mantle. Tri(i-decyl)amine (147.14 g) was then added. The mixture was warmed and dilute sulfuric acid (42.22 g concentrated $H_2SO_4$ plus 150.0 g deionized water) was added slowly to the phosphonic acid/molybdate/amine solution with stirring. The mixture was heated to reflux, with stirring, for 3 hours and then allowed to cool to room temperature. A dark blue syrup collected at the bottom of the flask, and the aqueous phase was decanted from the syrup and discarded. The syrup was rinsed twice with deionized water, hexane (200.0 g) was added, and the reactor was fitted with a Dean-Stark trap. The solution was heated to reflux, which was continued until all water had been removed by azeotropic distillation. The remaining solvent was removed by vacuum distillation. The dark blue syrup obtained was readily soluble in hexane and dicyclopentadiene, and the infrared spectrum was consistent with the structure $[(i-C_{10}H_{21})_3NH]_4\{(C_6H_5P)_2Mo_5O_{21}\}$.

Example 4

The procedure of Example 2 as essentially followed utilizing the amine tri(i-octyl)amine and a mixture of hexane/cyclohexane extraction solvent.

Sodium molybdate, $Na_2MoO_4.2H_2O$ (100.0 g), was dissolved in deionized water (400.0 g), and phenylphosphonic acid, $C_6H_5P(O)(OH)_2$ (26.14 g), was also dissolved in deionized water (100.0 g). The two solutions were combined in a 2 L round-bottom flask fitted with a water-cooled condenser and heating mantle. Tri(i-octyl)amine (117.38 g) was then added. The mixture was warmed and dilute sulfuric acid (42.22 g concentrated $H_2SO_4$ plus 150.0 g deionized water) was added slowly to the phosphonic acid/molybdate/amine solution with stirring. The mixture was heated to reflux, with stirring, for 3 hours and then allowed to cool to room temperature. A dark blue syrup collected at the bottom of the flask, and the aqueous phase was decanted from the syrup and discarded. The syrup was rinsed twice with deionized water, a blend of hexane (250.0 g) and cyclohexane (175.0 g) was added, and the reactor was fitted with a Dean-Stark trap. The solution was heated to reflux, which was continued until all water had been removed by azeotropic distillation. The remaining solvent was removed by vacuum distillation. The dark blue-green syrup obtained was readily soluble in cyclohexane and hot hexane. The infrared spectrum was consistent with the structure $[(i-C_8H_{17})_3NH]_4\{(C_6H_5P)_2Mo_5O_{21}\}$.

Example 5

The procedure of Example 2 was essentially followed utilizing the amine salt, tri(octyl)methylammonium chloride, and a cyclohexane extraction solvent.

Sodium molybdate, $Na_2MoO_4.2H_2O$ (100.0 g), was dissolved in deionized water (400.0 g), and phenylphosphonic acid, $C_6H_5P(O)(OH)_2$ (26.12 g), was also dissolved in deionized water (100.0 g). The two solutions were combined in a 2 L round-bottom flask fitted with a water-cooled condenser and heating mantle. Tri(i-octyl)methylammonium chloride (133.64 g) was then added. The mixture was warmed and dilute sulfuric acid (25.33 g concentrated $H_2SO_4$ plus 100.0 g deionized water) was added slowly to the phosphonic acid/molybdate/quaternary ammonium salt solution with stirring. The mixture was heated to reflux, with stirring, for 3 hours and then allowed to cool to room temperature. A dark green syrup collected at the bottom of the flask, and the aqueous phase was decanted from the syrup and discarded. The syrup was rinsed twice with deionized water, cyclohexane (300.0 g) was added, and the reactor was fitted with a Dean-Stark trap. The solution was heated to reflux, which was continued until all water had been removed by azeotropic distillation. The remaining solvent was removed by vacuum distillation. The dark syrup obtained was soluble in cyclohexane and and dicyclopentadiene, and the infrared spectrum was consistent with the structure $[(C_8H_{17})_3NCH_3]_4\{(C_6H_5P)_2Mo_5O_{21}\}$.

Example 6

The procedure of Example 2 was essentially followed utilizing the amine di(tridecyl)amine.

Sodium molybdate, $Na_2MoO_4.2H_2O$ (100.0 g), was dissolved in deionized water (400.0 g), and phenylphosphonic acid, $C_6H_5P(O)(OH)_2$ (26.12 g), was also dissolved in deionized water (100.0 g). The two solutions were combined in a 2 L round-bottom flask fitted with a water-cooled condenser and heating mantle. Di(tridodecyl)amine (129.75 g) was then added. The mixture was warmed and dilute sulfuric acid (42.22 g concentrated $H_2SO_4$ plus 150.0 g deionized water) was added slowly to the phosphonic acid/molybdate/amine mixture with stirring. The mixture was heated to reflux, with stirring, for 3 hours and then allowed to cool to room temperature. A dark blue solid "cake" formed at the bottom of the flask, and the aqueous phase was decanted from the syrup and discarded. The solid was rinsed twice with deionized water, and a mixture of cyclohexane (150.0 g) and hexane (100 g) was added. The reactor was fitted with a Dean-Stark trap, and the solution was heated to reflux and solvents were removed by vacuum distillation. The dark blue solid obtained was soluble in cyclohexane. Proposed structure: $[(C_{13}H_{27})_2NH_2]_4\{(C_6H_5P)_2Mo_5O_{21}\}$.

Example 7

Tri(hydrogenated tallow)amine was used in this example.

Sodium molybdate, $Na_2MoO_4. 2H_2O$ (16.02 g), was dissolved in deionized water (100.0 g), and phenylphosphonic acid, $C_6H_5P(O)(OH)_2$ (4.19 g), was also dissolved in deionized water (50.0 g). The two solutions were combined in an 1 L round-bottom flask fitted with a water-cooled condenser and heating mantle. Tri(hydrogenated tallow)amine (Adogen® 340, 40.0 g) was then added. The mixture was warmed and dilute sulfuric acid (6.77 g concentrated $H_2SO_4$ plus 50.0 g deionized water) was added slowly to the phosphonic acid/molybdate/amine suspension with stirring. The mixture was heated to reflux, with stirring, for 4 hours and then allowed to cool to room temperature. A dark blue solid "cake" formed at the bottom of the flask, and the aqueous phase was decanted from the solid and discarded. The solid was rinsed twice with deionized water, hexane (150.0 g) was added, and the reactor was fitted with a Dean-Stark trap. The solution was heated to reflux and continued until all water had been removed by azeotropic distillation. The remaining solvent was removed by vacuum distillation. The dark blue solid obtained was soluble in cyclohexane, hexane, and dicyclopentadiene, and the infrared spectrum was consistent with the structure $[(C_{18}H_{37})_{0.65}C_{16}H_{33})_{0.35}(C_{14}H_{29})_{0.05}NH]_4\{(C_6H_5P)_2Mo_5O_{21}\}$ (approximate ratios $C_{14}:C_{16}:C_{18}$).

Example 8

The procedure of Example 2 was essentially followed utilizing a different phosphonic acid (t-butyl phosphonic acid).

Sodium molybdate, $Na_2MoO_4 \cdot 2H_2O$ (21.90 g), was dissolved in deionized water (100.0 g), and t-butylphosphonic acid, $CH_3CP(O)(OH)_2$ (5.0 g), was also dissolved in deionized water (50.0 g). The two solutions were combined in an 1 L round-bottom flask fitted with a water-cooled condenser and heating mantle. Tridodecylamine (37.80 g) was then added. The mixture was warmed and dilute sulfuric acid (9.25 g concentrated $H_2SO_4$ plus 50.0 g deionized water) was added slowly to the phosphonic acid/molybdate/amine suspension with stirring. The mixture was heated to reflux, with stirring, for 3.5 hours and then allowed to cool to room temperature. A dark green syrup collected at the bottom of the flask, and the aqueous phase was decanted from the solid and discarded. The solid was rinsed twice with deionized water, a mixture of hexane (40.0 g) cyclohexane (100.0 g) was added, and the reactor was fitted with a Dean-Stark trap. The solution was heated to reflux which was continued until all water had been removed by azeotropic distillation. The remaining solvents were removed by vacuum distillation. The dark blue solid obtained was soluble in cyclohexane/hexane mixture. Proposed structure: $[(C_{12}H_{25})_3NH]_4\{(CH_3)_3CP)_2Mo_5O_{21}\}$.

Example 9

The tungstate was formed from a sodium tungstate utilizing the same phosphonic acid and ammonium nitrate of Example 2.

Sodium tungstate, $Na_2WO_4 \cdot 2H_2O$ (50.0 g), was dissolved in deionized water (200.0 g), and phenylphosphonic acid, $C_6H_5P(O)(OH)_2$ (9.59 g), was also dissolved in deionized water (100.0 g). The two solutions were combined in an 1 L round-bottom flask fitted with a water-cooled condenser and heating mantle. Tridodecylammonium nitrate (70.94 g) was then added. The mixture was warmed and dilute sulfuric acid (9.29 g concentrated $H_2SO_4$ plus 100.0 g deionized water) was added slowly to the phosphonic acid/tungstate/amine salt solution with stirring. The mixture was heated to reflux, with stirring, for 3.5 hours and then allowed to cool to room temperature. A yellow-amber syrup collected at the bottom of the flask, and the aqueous phase was decanted from the syrup and discarded. The syrup was rinsed twice with deionized water, hexane (150.0 g) was added, and the reactor was fitted with a Dean-Stark trap. The solution was heated to reflux which was continued until all water had been removed by azeotropic distillation. The remaining solvent was removed by vacuum distillation. The amber-colored syrup obtained was soluble in hexane and dicyclopentadiene. Proposed structure: $[(C_{12}H_{25})_3NH]_4\{(C_6H_5P)_2W_5O_{21}\}$.

Example 10

The procedure of Example 2 was essentially repeated utilizing tridodecylamine instead of the salt thereof.

Sodium molybdate, $Na_2MoO_4 \cdot 2H_2O$ (100.0 g), was dissolved in deionized water (400.0 g), and phenylphosphonic acid, $C_6H_5P(O)(OH)_2$ (26.12 g), was also dissolved in deionized water (100.0 g). The two solutions were combined in a 2 L round-bottom flask fitted with a water-cooled condenser and heating mantle. Tridodecylamine (172.56 g) was then added. The mixture was warmed and dilute sulfuric acid (42.22 g concentrated $H_2SO_4$ plus 100.0 g deionized water) was added slowly to the phosphonic acid/molybdate/amine mixture with stirring. The mixture was heated to reflux, with stirring, for 3 hours and then allowed to cool to room temperature. A dark green syrup collected at the bottom of the flask, and the aqueous phase was decanted from the syrup and discarded. The syrup was rinsed twice with deionized water, hexane (250.0 g) was added, and the reactor was fitted with a Dean-Stark trap. The solution was heated to reflux and continued until all water had been removed by azeotropic distillation. The remaining hexane was removed by vacuum distillation. The dark green syrup obtained was readily soluble in hexane and dicyclopentadiene, and the infrared spectrum was consistent with the structure $[(C_{12}H_{25})_3NH]_4\{(C_6H_5P)_2Mo_5O_{21}\}$.

Example 11

The procedure of Example 10 was essentially followed utilizing a different acid, phenylphosphinic acid.

Sodium molybdate, $Na_2MoO_4 \cdot 2H_2O$ (100.0 g), was dissolved in deionized water (400.0 g), and phenylphosphinic acid, $C_6H_5P(O)(OH)(H)$ (23.49 g), was also dissolved in deionized water (75 g). The two solutions were combined in a 2 L round-bottom flask fitted with a water-cooled condenser and heating mantle. Tridodecylamine (172.56 g) was then added. The mixture was warmed and dilute sulfuric acid (42.22 g concentrated $H_2SO_4$ plus 100.0 g deionized water) was added slowly to the phosphinic acid/molybdate/amine mixture with stirring. The mixture was heated to reflux, with stirring, for 3.5 hours and then allowed to cool to room temperature. A dark blue syrup collected at the bottom of the flask, and the aqueous phase was decanted from the syrup and discarded. The syrup was rinsed twice with deionized water, hexane (350.0 g) was added, and the reactor was fitted with a Dean-Stark trap. The solution was heated to reflux, which was continued until all water had been removed by azeotropic distillation. The remaining hexane was removed by vacuum distillation. The dark green syrup obtained was readily soluble in hexane and dicyclopentadiene.

Example 12

The procedure of Example 10 was essentially followed utilizing a phosphate disodiumphenylphosphate instead of phenylphosphonic acid.

Sodium molybdate, $Na_2MoO_4 \cdot 2H_2O$ (50.0 g), was dissolved in deionized water (400.0 g), and disodiumphenylphosphate, $C_6H_5OP(O)(ONa)_2 \cdot 2H_2O$ (21.0 g), was also dissolved in deionized water (100.0 g). The two solutions were combined in an 1 L round-bottom flask fitted with a water-cooled condenser and heating mantle. Tridodecylamine (86.3 g) was then added. The mixture was warmed and dilute sulfuric acid (29.56 g concentrated $H_2SO_4$ plus 100.0 g deionized water) was added slowly to the phosphonate/molybdate/amine mixture with stirring. The mixture was heated to reflux, with stirring, for 3 hours and then allowed to cool to room temperature. A dark blue syrup collected at the bottom of the flask, and the aqueous phase was decanted from the syrup and discarded. The syrup was rinsed twice with deionized water, hexane (225 g) was added, and the reactor was fitted with a Dean-Stark trap. The solution was heated to reflux and continued until all water had been removed by azeotropic distillation. The remaining hexane was removed by vacuum distillation. The dark blue syrup obtained was readily soluble in hexane and dicyclopentadiene. Proposed structure: $[(C_{12}H_{25})_3NH]_4\{(C_6H_5OP)_2Mo_5O_{21}\}$.

Example 13

The procedure of Example 10 was essentially followed, replacing the phenylphosphonic acid with disodium(glycerol-2-phosphate).

Sodium molybdate, $Na_2MoO_4 \cdot 2H_2O$ (50.0 g), was dissolved in deionized water (200.0 g), and disodium(glycerol-2-phosphate), $(HOCH_2CHOP(O)(ONa)_2$ (21.0 g), was also dissolved in deionized water (100.0 g). The two solutions were combined in an 1 L round-bottom flask fitted with a water-cooled condenser and heating mantle. Tridodecylamine (86.3 g) was then added. The mixture was warmed and dilute sulfuric acid (29.6 g concentrated $H_2SO_4$ plus 100.0 g deionized water) was added slowly to the phosphate/molybdate/amine mixture with stirring. The mixture was heated to reflux, with stirring, for 3 hours and then allowed to cool to room temperature. A dark blue syrup collected at the bottom of the flask, and the aqueous phase was decanted from the syrup and discarded. The syrup was rinsed twice with deionized water, hexane (225 g) was added, and the reactor was fined with a Dean-Stark trap. The solution was heated to reflux, which was continued until all water had been removed by azeotropic distillation. The remaining solvent was removed by vacuum distillation. The dark blue syrup obtained was readily soluble in hexane and dicyclopentadiene. Proposed structure: $[(C_{12}H_{25})_3NH]_4\{[(HOCH_2)_2CHOP]_2Mo_5O_{21}\}$.

Example 14

The phosphonic acid used in this example was 2-carboxyethylphosphonic acid.

Sodium molybdate, $Na_2MoO_4 \cdot 2H_2O$ (38.87 g), was dissolved in deionized water (150.0 g), and 2-carboxyethylphosphonic acid $HOC(O)CH_2P(O)(OH)_2$ (9.9 g), was also dissolved in deionized water (75 g). The two solutions were combined in a 1 L round-bottom flask fined with a water-cooled condenser and heating mantle. Tridodecylamine (67.09 g) was then added. The mixture was warmed and dilute sulfuric acid (16.41 g concentrated $H_2SO_4$ plus 100.0 g deionized water) was added slowly to the phosphonic acid/molybdate/amine mixture with stirring. The mixture was heated to reflux, with stirring, for 2 hours and then allowed to cool to room temperature. A dark green syrup collected at the bottom of the flask, and the aqueous phase was decanted from the syrup and discarded. The syrup was rinsed twice with deionized water, hexane (225 g) was added, and the reactor was fitted with a Dean-Stark trap. The solution was heated to reflux, which was continued until all water had been removed by azeotropic distillation. The remaining hexane was removed by vacuum distillation. Proposed structure:

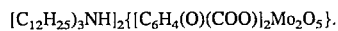

$[C_{12}H_{25})_3NH]_2\{[C_6H_4(O)(COO)]_2Mo_2O_5\}$.

Example 15

The procedure of Example 10 was essentially followed utilizing a different phosphonic acid, methylphosphonic acid.

Sodium molybdate, $Na_2MoO_4 \cdot 2H_2O$ (32.38 g), was dissolved in deionized water (100.0 g), and methylphosphonic acid, $CH_3CP(O)(OH)_2$ (5.14 g), was also dissolved in deionized water (50.0 g). The two solutions were combined in a 1 L round-bottom flask fitted with a water-cooled condenser and heating mantle. Tridodecylamine (55.89 g) was then added. The mixture was warmed and dilute sulfuric acid (13.67 g concentrated $H_2SO_4$ plus 75 g deionized water) was added slowly to the phosphonic acid/molybdate/amine suspension with stirring. The mixture was heated to reflux, with stirring, for 3 hours and then allowed to cool to room temperature. A dark blue-green syrup collected at the bottom of the flask, and the aqueous phase was decanted from the solid and discarded. The solid was rinsed twice with deionized water, hexane (200.0 g) was added, and the reactor was fitted with a Dean-Stark trap. The solution was heated to reflux and continued until all water had been removed by azeotropic distillation. The remaining solvent was removed by vacuum distillation. The dark blue-green syrup obtained was soluble in cyclohexane and hot hexane. Proposed structure: $[(C_{12}H_{25})_3NH]_4\{(CH_3P)_2Mo_5O_{21}\}$.

Example 16

The procedure of Example 10 was essentially followed utilizing animophenylphosphonic acid instead of phenylphosphonic acid.

Sodium molybdate, $Na_2MoO_4 \cdot 2H_2O$ (20.37 g), was dissolved in deionized water (150.0 g), and aminophenylphosphonic acid, $H_2NC_6H_4P(O)(OH)_2$ (5.83 g), was suspended in deionized water (50.0 g). The two solutions were combined in an 1 L round-bottom flask fitted with a water-cooled condenser and heating mantle. Tridodecylamine (17.58 g) was then added. The mixture was warmed and dilute sulfuric acid (8.64 g concentrated $H_2SO_4$ plus 50.0 g deionized water) was added slowly to the suspension with stirring. The mixture was heated to reflux, with stirring, for 2 hours and then allowed to cool. A dark blue-green semi-solid cake formed at the bottom of the flask, and the aqueous phase was decanted. The solid was rinsed twice with deionized water, hexane (150.0 g) was added, and the reactor was fitted with a Dean-Stark trap. The solution was heated to reflux, which was continued until all water had been removed by azeotropic distillation. The remaining solvent was removed by vacuum distillation. The dark blue-green syrup obtained was soluble in cyclohexane and hexane. Proposed structure: $[(C_{12}H_{25})_3NH]_2\{(H_3N\,C_6H_4P)_2Mo_5O_{21}\}$.

Example 17

The procedure of Example 10 was essentially repeated utilizing a different phosphonic acid, butylphosphonic acid.

Sodium molybdate, $Na_2MoO_4 \cdot 2H_2O$ (22.60 g), was dissolved in deionized water (100.0 g), and butylphosphonic acid, $C_4H_9P(O)(OH)_2$ (5.16 g), was also dissolved in deionized water (50.0 g). The two solutions were combined in an 1 L round-bottom flask fitted with a water-cooled condenser and heating mantle. Tridodecylamine (39.0 g) was then added. The mixture was warmed and dilute sulfuric acid (9.55 g concentrated $H_2SO_4$ plus 75 g deionized water) was added slowly to the phosphonic acid/molybdate/amine suspension with stirring. The mixture was heated to reflux, with stirring, for 3 hours and then allowed to cool to room temperature. A dark blue-green syrup collected at the bottom of the flask, and the aqueous phase was decanted from the syrup and discarded. The syrup was rinsed twice with deionized water, hexane (200.0 g) was added, and the reactor was fitted with a Dean-Stark trap. The solution was heated to reflux and continued until all water had been removed by azeotropic distillation. The remaining solvent was removed by vacuum distillation. The dark blue-green syrup obtained was readily soluble in cyclohexane and hot hexane. Proposed structure $[(C_{12}H_{25})_3NH]_4\{(C_4H_9P)_2Mo_5O_{21}\}$.

Example 18

The procedure of Example 10 was essentially followed utilizing the phosphonic acid methylenediphosphonic acid.

Sodium molybdate, $Na_2MoO_4.2H_2O$ (7.7 g), was dissolved in deionized water (75 g), and methylenediphosphonic acid, $CH_2[P(O)(OH)_2]_2$ (1.13 g), was also dissolved in deionized water (50.0 g). The two solutions were combined in a 500 ml round-bottom flask fitted with a water-cooled condenser and heating mantle. Tridodecylamine (13.41 g) was then added. The mixture was warmed and dilute sulfuric acid (3.28 g concentrated $H_2SO_4$ plus 50.0 g deionized water) was added slowly to the diphosphonic acid/molybdate/amine suspension with stirring. The mixture was heated to reflux, with stirring, for 90 minutes and then allowed to cool to room temperature. A green syrup collected at the bottom of the flask, and the aqueous phase was decanted from the syrup and discarded. The solid was rinsed twice with deionized water, hexane (200.0 g) was added, and the reactor was fitted with a Dean-Stark trap. The solution was heated to reflux and continued until all water had been removed by azeotropic distillation. The remaining solvent was removed by vacuum distillation. The green syrup obtained was soluble in hexane.

Example 19

Ammonium heptamolybdate, $(NH_4)_6Mo_7O_{24}.4H_2O$ (100.0 g), was dissolved in deionized water (500.0 g), and phenylphosphonic acid, $C_6H_5P(O)(OH)_2$ (35.82 g), was also added to the heptamolybdate solution. The solution was tranferred to a 2 L round-bottom flask fitted with a water-cooled condenser and heating mantle. Tridodecylamine (236.5 g) was then added. The mixture was warmed and dilute sulfuric acid (24.80 g concentrated $H_2SO_4$ plus 150.0 g deionized water) was added slowly to the phosphonic acid/molybdate/amine solution with stirring. The mixture was heated to reflux, with stirring, for 90 minutes and then allowed to cool to room temperature. A dark green syrup collected at the bottom of the flask, and the aqueous phase was decanted from the syrup and discarded. The syrup was rinsed twice with deionized water, hexane (250.0 g) was added, and the reactor was fitted with a Dean-Stark trap. The solution was heated to reflux and continued until all water had been removed by azeotropic distillation. The remaining solvent was removed by vacuum distillation. The dark green syrup obtained was readily soluble in hexane and dicyclopentadiene, and the infrared spectrum was consistent with the structure $[(C_{12}H_{25})_3NH]_4\{(C_6H_5P)_2Mo_5O_{21}\}$.

Example 20

Ammonium heptamolybdate, $(NH_4)_6Mo_7O_{24}.4H_2O$ (50.0 g), was dissolved in deionized water (300.0 g), and phosphorus acid, $H_3PO_3$ (9.29 g), was then added to the heptamolybdate solution. The solution was tranferred to an 1 L round-bottom flask fitted with a water-cooled condenser and heating mantle. Tridodecylamine (118.45 g) was then added. The mixture was warmed and dilute sulfuric acid (12.40 g concentrated $H_2SO_4$ plus 100.0 g deionized water) was added slowly to the phosphorus acid/heptamolybdate/amine suspension with stirring. The mixture was heated to reflux, with stirring, for 5 hours and then allowed to cool to room temperature. A dark blue-green syrup collected at the bottom of the flask, and the aqueous phase was decanted from the solid and discarded. The solid was rinsed twice with deionized water, hexane (200.0 g) was added, and the reactor was fitted with a Dean-Stark trap. The solution was heated to reflux and continued until all water had been removed by azeotropic distillation. The remaining solvent was removed by vacuum distillation. The dark blue-green syrup obtained was soluble in cyclohexane and hexane. Proposed structure: $[(C_{12}H_{25})_3NH]_4\{(HP)_2Mo_5O_{21}\}$.

Example 21

Sodium molybdate $Na_2MoO_4.2H_2O$ (100.0 g), was dissolved in deionized water (400.0 g), and phenylphosphonic acid, $C_6H_5P(O)(OH)_2$ (26.12 g), was also dissolved in deionized water (100.0 g). The two solutions were combined in a 2 L round-bottom flask fitted with a water-cooled condenser and heating mantle. Di(tridecyl)amine (129.75 g) was then added. The mixture was warmed and dilute sulfuric acid (42.2 g concentrated $H_2SO_4$ plus 150.0 g deionized water) was added slowly to the phosphonic acid/molybdate/amine mixture with stirring. The mixture was heated to reflux, with stirring, for 3 hours and then allowed to cool to room temperature. A dark blue solid "cake" formed at the bottom of the flask, and the aqueous phase was decanted from the syrup and discarded. The solid was rinsed twice with deionized water, and a mixture of cyclohexane (150.0 g) and hexane (100.0 g) was added. The reactor was fitted with a Dean-Stark trap and the solution was heated to reflux and continued until all water had been removed by azeotropic distillation. The remaining solvents were removed by vacuum distillation. The dark blue solid obtained was soluble in cyclohexane. Proposed structure $[(C_{13}H_{27})_2NH_2]_4\{(C_6H_5P)_2MO_5O_2\}$.

Example 22

Ammonium heptamolybdate, $(NH_4)_6Mo_7O_{24}.4H_2O$ (100.0 g), was dissolved in deionized water (600.0 g), and lactic acid, $CH_3CH(OH)(COOH)$ (30.01 g of 85 percent solution in $H_2O$ plus 100.0 grams of additional $H_2O$) was then added to the heptamolybdate solution. The solution was tranferred to a 2 L round-bottom flask fitted with a water-cooled condenser and heating mantle. Tridodecylamine (295.7 g) was then added. The mixture was warmed and dilute sulfuric acid (24.79 g concentrated $H_2SO_4$ plus 75 g deionized water) was added slowly to the lactic acid/molybdate/amine suspension with stirring. The mixture was heated to reflux, with stirring, for 5 hours and then allowed to cool to room temperature. A dark blue-green syrup collected at the bottom of the flask, and the aqueous phase was decanted from the solid and discarded. The solid was rinsed twice with deionized water, hexane (500.0 g) was added and the reactor was fitted with a Dean-Stark trap. The solution was heated to reflux which was continued until all water had been removed by azeotropic distillation. The remaining solvent was removed by vacuum distillation. The dark blue-green syrup obtained was soluble in cyclohexane and hexane. Approximate structure: $[(C_{12}H_{25})_3NH]_4\{[CH_3CH(O)(COO)]_2Mo_4O_{12}\}$.

Example 23

Molybdenum trioxide, $MoO_3$ (50.0 g) was suspended in a solution of deionized water (400.0 g), and lactic acid, $CH_3CH(OH)(COOH)$ (18.41 g of 85 percent solution in $H_2O$). The solution was tranferred to an 1 L round-bottom flask fitted with a water-cooled condenser and heating mantle. Tridodecylamine (181.36 g) was then added and the mixture was heated to reflux, with stirring, for 6 hours and then allowed to cool to room temperature. A dark blue-green syrup collected at the bottom of the flask and the aqueous phase was decanted from the solid and discarded. The solid was rinsed twice with deionized water, hexane (250.0 g) was added and the reactor was fitted with a Dean-Stark trap. The solution was heated to reflux which was continued until all water had been removed by azeotropic distillation. The remaining solvent was removed by vacuum distillation. The dark blue-green syrup obtained was soluble in cyclohexane and hexane. Approximate structure: $[(C_{12}H_{25})_3NH]_2\{[CH_3CH(O)(COO)]_2Mo_2O_5\}$.

Example 24

Sodium molybdate $Na_2MoO_4 \cdot 2H_2O$ (24.20 g), was dissolved in deionized water (300.0 g), and salicylic acid, $1,2-C_6H_4(OH)(COOH)$ (27.63 g), was then added to the heptamolybdate solution. The solution was transferred to an 1 L round-bottom flask fitted with a water-cooled condenser and heating mantle. Tridodecylamine (104.42 g) was then added. The mixture was warmed and dilute sulfuric acid (10.22 g concentrated $H_2SO_4$ plus 50.0 g deionized water) was added slowly to the salicylic acid/heptamolybdate/amine suspension with stirring. The mixture was heated to reflux, with stirring, for 3 hours and then allowed to cool to room temperature. A dark green syrup collected at the bottom of the flask, and the aqueous phase was decanted from the syrup and discarded. The solid was rinsed twice with deionized water, hexane (250.0 g) was added and the reactor was fitted with a Dean-Stark trap. The solution was heated to reflux and continued until all water had been removed by azeotropic distillation. The remaining solvents were removed by vacuum distillation. The dark blue-green syrup was soluble in cyclohexane and hexane. Approximate structure $[(C_{12}H_{25})_3NH]_2\{[C_6H_4(O)(COO)]_2Mo_5O_2\}$.

Example 25

Ammonium heptamolybdate, $(NH_4)_6Mo_7O_{24} \cdot 4H_2O$ (25.0 g), was dissolved in deionized water (300.0 g), and salicylic acid, $1,2-C_6H_4(OH)(COOH)$ (19.56 g) was then added to the heptamolybdate solution. The solution was tranferred to an 1 L round-bottom flask with a water-cooled condenser and heating mantle. Tridodecylamine (73.92 g) was then added. The mixture was warmed and dilute sulfuric acid (6.20 g concentrated $H_2SO_4$ plus 50.0 g deionized water) was added slowly to the salicylic acid/molybdate/amine suspension with stirring. The mixture was heated to reflux, with stirring, for 3 hours and then allowed to cool to room temperature. A dark green syrup collected at the bottom of the flask, and the aqueous phase was decanted from the solid and discarded. The solid was rinsed twice with deionized water, hexane (250.0 g) was added and the reactor was fitted with a Dean-Stark trap. The solution was heated to reflux which was continued until all water had been removed by azeotropic distillation. The remaining solvent was removed by vacuum distillation. The dark blue-green syrup obtained was soluble in cyclohexane and hexane. Approximate structure: $[(C_{12}H_{25})_3NH]_2\{[C_6H_4(O)(COO)]_2Mo_2O_5\}$.

Example 26

Ammonium heptamolybdate, $(NH_4)_6Mo_7O_{24} \cdot 4H_2O$ (50.0 g) was dissolved in deionized water (300.0 g), and salicylic acid, $1,2-C_6H_4(OH)(COOH)$ (19.58 g) was then added to the heptamolybdate solution. The solution was tranferred to an 1 L round-bottom flask fitted with a water-cooled condenser and heating mantle. Tridodecylamine (148.0 g) was then added. The mixture was warmed and dilute sulfuric acid (12.41 g concentrated $H_2SO_4$ plus 500 g deionized water) was added slowly to the salicylic acid/molybdate/amine suspension with stirring. The mixture was heated to reflux, with stirring, for 3 hours and then allowed to cool to room temperature. A dark green syrup collected at the bottom of the flask, and the aqueous phase was decanted from the solid and discarded. The solid was rinsed twice with deionized water, hexane (250.0 g) was added and the reactor was fitted with a Dean-Stark trap. The solution was heated to reflux which was continued until all water had been removed by azeotropic distillation. The remaining solvent was removed by vacuum distillation. The dark blue-green syrup obtained was soluble in cyclohexane and hexane. Approximate structure: $[(C_{12}H_{25})_3NH]_4\{[C_6H_4(O)(COO)]_2Mo_4O_{12}\}$.

Example 27

Ammonium heptamolybdate, $(NH_4)_6Mo_7O_{24} \cdot 4H_2O$ (25.0 g) was dissolved in deionized water (300.0 g) and tranferred to an 1 L round-bottom flask fitted with a water-cooled condenser and heating mantle. 1-hydroxy-2-naphthoic acid, $C_{10}H_6(OH)(COOH)$ (26.65 g) was then added to the heptamolybdate solution. Tridodecylamine (73.92 g) was then added. The mixture was warmed and dilute sulfuric acid (6.20 g concentrated $H_2SO_4$ plus 50.0 g deionized water) was added slowly to the 1-hydroxy-2-naphthoic acid/molybdate/amine suspension with stirring. The mixture was heated to reflux, with stirring, for 3 hours and then allowed to cool to room temperature. A dark green syrup collected at the bottom of the flask, and the aqueous phase was decanted from the solid and discarded. The solid was rinsed twice with deionized water, hexane (290.0 g) was added and the reactor was fitted with a Dean-Stark trap. The solution was heated to reflux which was continued until all water had been removed by azeotropic distillation. The remaining solvent was removed by vacuum distillation. The dark blue-green syrup obtained was soluble in cyclohexane and hexane. Approximate structure: $[(C_{12}H_{25})_3NH]_2\{[C_{10}H_6(O)(COO)]_2Mo_2O_5\}$.

Example 28

Ammonium heptamolybdate, $(NH_4)_6Mo_7O_{24} \cdot 4H_2O$ (25.0 g) was dissolved in deionized water (300.0 g) and tranferred to an 1 L round-bottom flask fitted with a water-cooled condenser and heating mantle. 4-methylsalicylic acid, $CH_3C_6H_3(OH)(COOH)$ (21.54 g) was then added to the heptamolybdate solution. Tridodecylamine (73.92 g) was then added. The mixture was warmed and dilute sulfuric acid (6.20 g concentrated $H_2SO_4$ plus 50.0 g deionized water) was added slowly to the methylsalicylic acid/molybdate/amine suspension with stirring. The mixture was heated to reflux, with stirring, for 3 hours and then allowed to cool to room temperature. A dark green syrup collected at the bottom of the flask and the aqueous phase was decanted from the solid and discarded. The solid was rinsed twice with deionized water, hexane (290.0 g) was added and the reactor was fitted with a Dean-Stark trap. The solution was heated to reflux which was continued until all water had been removed by azeotropic distillation. The remaining solvent was removed by vacuum distillation. The dark blue-green syrup obtained was soluble in cyclohexane and hexane. Approximate structure: $[(C_{12}H_{25})_3NH]_2\{[CH_3C_6H_3(O)(COO)]_2Mo_2O_5\}$.

Example 29

Ammonium heptamolybdate, $(NH_4)_6Mo_7O_{24} \cdot 4H_2O$ (6.24 g) was dissolved in deionized water (150.0 g) and tranferred to a 500 ml round-bottom flask fined with a water-cooled condenser and heating mantle. 3,5-dibromosalicylic acid, $Br_2-C_6H_2(OH)(COOH)$ (10.48 g) was then added to the heptamolybdate solution. Tridodecylamine (18.48 g) was then added. The mixture was warmed and dilute sulfuric acid (1.55 g concentrated $H_2SO_4$ plus 30.0 g deionized water) was added slowly to the dibromosalicylic acid/molybdate/amine suspension with stirring. The mixture was heated to reflux, with stirring, for 3 hours and then allowed to cool to room temperature. A yellow syrup collected at the bottom of the flask and the aqueous phase was decanted from the solid and discarded. The syrup was rinsed twice with deionized water, hexane (150.0 g) was added and the reactor was fined with a Dean-Stark trap. The solution was heated to reflux which was continued until all water had been removed by azeotropic distillation. The remaining solvent was removed by vacuum distillation. The yellow syrup obtained was soluble in cyclohexane and hexane. Approximate structure: $[(C_{12}H_{25})_3NH]_2\{[Br_2C_6H_2(O)(COO)]_2MoO_2\}$.

Example 30

Ammonium heptamolybdate, $(NH_4)_6Mo_7O_{24} \cdot 4H_2O$ (45.0 g) was dissolved in deionized water (270.0 g) and malic acid, $(HOOC)CH_2CH(OH)(COOH)$ (17.1 g in 45 g. $H_2O$ was then added to the heptamolybdate solution. The solution was tranferred to an 1 L round-bottom flask fined with a water-cooled condenser and heating mantle. Tridodecylamine (133.22 g) was then added. The mixture was warmed and dilute sulfuric acid (11.17 g concentrated $H_2SO_4$ plus 34 g deionized water) was added slowly to the malic acid/molybdate/amine suspension with stirring. The mixture was heated to reflux, with stirring, for 4 hours and then allowed to cool to room temperature. A dark blue-green syrup collected at the bottom of the flask and the aqueous phase was decanted from the solid and discarded. The syrup was rinsed twice with deionized water, hexane (200.0 g) was added and the reactor was fitted with a Dean-Stark trap. The solution was heated to reflux which was continued until all water had been removed by azeotropic distillation. The remaining solvent was removed by vacuum distillation. The dark blue-green syrup obtained was soluble in cyclohexane and hexane. Proposed structure: $[(C_{12}H_{25})_3NH]_2\{[(OOC)CH_2CH(O)(COO)]_2Mo_4O_{12}\}$.

Example 31

Ammonium heptamolybdate, $(NH_4)_6Mo_7O_{24} \cdot 4H_2O$ (25.0 g) was dissolved in deionized water (400.0 g) and tranferred to an 1 L round-bottom flask fitted with a water-cooled condenser and heating mantle. Tridodecylamine (73.93 g) was then added. Citric acid, $(HOOC)CH_2CH(OH)(COOH)CH_2(COOH)$ (14.88 g in 100.0 g $H_2O$) was then added chopwise to the molybdate/amine mixture. The mixture was heated to reflux, with stirring, for 3 hours and then allowed to cool to room temperature. A dark green syrup collected at the bottom of the flask and the aqueous phase was decanted from the solid and discarded. The solid was rinsed twice with deionized water, cyclohexane (300.0 g) was added and the reactor was fitted with a Dean-Stark trap. The solution was heated to reflux which was continued until all water had been removed by azeotropic distillation. The remaining solvent was removed by vacuum distillation. The dark green syrup obtained was soluble in cyclohexane and hexane.

Example 32

Molybdenum trioxide, $MoO_3$ (25.0 g) was suspended in a solution of deionized water (250.0 g). Catechol, $C_6H_4(OH)_2$ was added to an 1 L round-bottomed flask fitted with a water-cooled condenser and heating mantle and the molybdate suspension was transferred to the flask. Tridodecylamine (181.32 g) was then added and the mixture was heated to reflux, with stirring, for 3 hours and then allowed to cool to room temperature. A dark red-orange syrup collected at the bottom of the flask and the aqueous phase was decanted from the solid and discarded. The solid was rinsed twice with deionized water, cyclohexane (280.0 g), was added and the reactor was fitted with a Dean-Stark trap. The solution was heated to reflux which was continued until all water had been removed by azeotropic distillation. The remaining solvent was removed by vacuum distillation. The dark red-orange syrup obtained was soluble in cyclohexane. Approximate structure: $[(C_{12}H_{25})_3NH]_2\{(C_6H_4O_2)_2MoO_2\}$.

Example 33

Phenylphosphonic acid, $C_6H_5P(O)(OH)_2$ (43.94 g) was dissolved in deionized water (800.0 g) in a 2 L round-bottomed flask fitted with a water-cooled condenser and heating mantle. Molybdenum trioxide, $MoO_3$ (100.0 g) was added carefully to the phosphonic acid solution to avoid agglomeration. Tridodecylamine (290.12 g) was then added. The mixture was heated to reflux, with stirring, for 3 hours and then allowed to cool to room temperature. A dark blue-green syrup collected at the bottom of the flask and the aqueous phase was decanted from the solid and discarded. The solid was rinsed twice with deionized water, hexane (300.0 g) was added and the reactor was fitted with a Dean-Stark trap. The solution was heated to reflux which was continued until all water had been removed by azeotropic distillation. The remaining solvent was removed by vacuum distillation. The dark blue-green syrup obtained was soluble in cyclohexane and hexane. Proposed structure: $[(C_{12}H_{25})_3NH]_4\{(C_6H_5P)_2Mo_5O_{21}\}$.

Example 34

Ammonium sulfate $(NH_4)_2SO_4$ (18.35 g) and phenylphosphonic acid $C_6H_5P(O)(OH)_2$ (43.94 g) were dissolved in deionized water (800.0 g) and the solution was transferred to a 2 L round-bottomed flask fitted with a water-cooled condenser and heating mantle. Molybdenum trioxide, $MoO_3$ (100.0 g) was added carefully to the ammonium sulfate/phosphonic acid solution to avoid agglomeration. Tridodecylumine (290.12 g) was then added. The mixture was heated to reflux, with stirring, for 4 hours and then allowed to cool to room temperature. A dark blue-green syrup collected at the bottom of the flask and the aqueous phase was decanted from the solid and discarded. The solid was rinsed twice with deionized water, hexane (300.0 g) was added and the reactor was fitted with a Dean-Stark trap. The solution was heated to reflux which was continued until all water had been removed by azeotropic distillation. The remaining solvent was removed by vacuum distillation. The dark blue-green syrup obtained was soluble in cyclohexane and hexane. Proposed structure: $[(C_{12}H_{25})_3NH]_4\{(C_6H_5P)_2Mo_5O_{21}\}$.

Example 35

Ammonium dimolybdate $NH_4)_2Mo_2O_7$ (100.0 g) was dissolved in deionized water (550.0 g) and phenylphosphonic acid, $C_6H_5P(O)(OH)_2$ (43.90 g) was then added to the dimolybdate solution. The solution was transferred to a 2 L round-bottomed flask fitted with a water-cooled condenser and heating mantle. Tridodecylamine (245.74 g) was then added. The mixture was warmed and dilute sulfuric acid (30.06 g concentrated $H_2SO_4$ plus 150.0 g deionized water) was added slowly to the phosphonic acid/molybdate/amine suspension with stirring. The mixture was heated to reflux, with stirring, for 2 hours and then allowed to cool to room temperature. A dark blue-green syrup collected at the bottom of the flask and the aqueous phase was decanted from the solid and discarded. The solid was rinsed twice with deionized water, hexane (300.0 g) was added and the reactor was fitted with a Dean-Stark trap. The solution was heated to reflux which was continued until all water had been removed by azeotropic distillation. The remaining solvent was removed by vacuum distillation. The dark blue-green syrup obtained was soluble in cyclohexane and hexane. Proposed structure: $[(C_{12}H_{25})_3NH]_4\{(C_6H_5P)_2Mo_5O_{21}\}$.

Example 36

Phosphorus acid $H_3PO_3$ (11.4 g) was dissolved in deionized water (400.0 g) in an 1 L round-bottomed flask fitted with a water-cooled condenser and heating mantle. Molybdenum trioxide, $MoO_3$ (50.0 g) was added carefully to the phosphorus acid solution to avoid agglomeration. Tridodecylamine (145.13 g) was then added. The mixture was heated to reflux, with stirring, for 3 hours and then allowed to cool to room temperature. A dark blue-green syrup collected at the bottom of the flask and the aqueous phase was decanted from the solid and discarded. The solid was rinsed twice with deionized water, hexane (200.0 g) was added and the reactor was fitted with a Dean-Stark trap. The solution was heated to reflux which was continued until all water had been removed by azeotropic distillation. The remaining solvent was removed by vacuum distillation. The dark blue-green syrup obtained was soluble in cyclohexane and hexane. Proposed structure: $[(C_{12}H_{25})_3NH]_4\{(HP)_2Mo_5O_{21}\}$.

Example 37

Ammonium sulfate $(NH_4)_2SO_4$ (10.0 g) and phosphorus acid $H_3PO$ (11.4 g) were dissolved in deionized water (400.0 g) and the solution was transferred to an 1 L round-bottomed flask fitted with a water-cooled condenser and heating mantle. $MoO_3$ (50.0 g) was added carefully to the ammonium sulfate/phosphorus acid solution to avoid agglomeration. Tridodecylamine (145.13 g) was then added. The mixture was heated to reflux, with stirring, for 3 hours and then allowed to cool to room temperature. A dark blue-green syrup collected at the bottom of the flask and the aqueous phase was decanted from the solid and discarded. The solid was rinsed twice with deionized water, hexane (200.0 g) was added and the reactor was fitted with a Dean-Stark trap. The solution was heated to reflux which was continued until all water had been removed by azeotropic distillation. The remaining solvent was removed by vacuum distillation. The dark blue-green syrup obtained was soluble in cyclohexane and hexane. Proposed structure: $[(C_{12}H_{25})_3NH]_4\{(HP)_2Mo_5O_{21}\}$.

Example 38

Phosphorus acid $H_3PO_4$ (16.02 g) was dissolved in deionized water (400.0 g) in an 1 L round-bottomed flask fired with a water-cooled condenser and heating mantle. Molybdenum trioxide, $MoO_3$ (50.0 g) was added carefully to the phosphoric acid solution to avoid agglomeration. Tridodecylamine (145.13 g) was then added. The mixture was heated to reflux, with stirring, for 4 hours and then allowed to cool to room temperature. A dark blue-green syrup collected at the bottom of the flask and the aqueous phase was decanted from the solid and discarded. The solid was rinsed twice with deionized water, hexane (200.0 g) was added and the reactor was fitted with a Dean-Stark trap. The solution was heated to reflux which was continued until all water had been removed by azeotropic distillation. The remaining solvent was removed by vacuum distillation. The dark blue-green syrup obtained was soluble in cyclohexane and hexane. Proposed structure: $[(C_{12}H_{25})_3NH]_4\{(HOP)_2Mo_5O_{21}\}$.

Example 39

Ammonium sulfate $(NH_4)_2SO_4$ (10.0 g) and phosphoric acid $H_3PO_4$ (16.02 g) were dissolved in deionized water (400.0 g) and the solution was transferred to an 1 L round-bottomed flask fitted with a water-cooled condenser and heating mantle. Molybdenum trioxide, $MoO_3$ (50.0 g) was added carefully to the ammonium sulfate/phosphoric acid solution to avoid agglomeration. Tridodecylamine (145.13 g) was then added. The mixture was heated to reflux, with stirring, for 4 hours and then allowed to cool to room temperature. A dark blue-green syrup collected at the bottom of the flask and the aqueous phase was decanted from the solid and discarded. The solid was rinsed twice with deionized water, hexane (200.0 g) was added and the reactor was fired with a Dean-Stark trap. The solution was heated to reflux which was continued until all water had been removed by azeotropic distillation. The remaining solvent was removed by vacuum distillation. The dark blue-green syrup obtained was soluble in cyclohexane and hexane. Proposed structure: $[(C_{12}H_{25})_3NH]_4\{(HOP)_2Mo_5O_{21}\}$.

Catalytic Activity Tests

The ligated polyoxomolybdate produced in Examples 1–4 were tested for their activity in polymerizing dicyclopentadiene under conditions of a RIM procedure.

Reaction injection molding components were prepared with the following recipes: Component A contained 88.2 wt. percent dicyclopentadiene/7.17 wt. percent cyclopentadiene trimer/3.52 wt. percent butadiene elastomer/0.5 wt. percent diethylaluminumchloride/0.25 wt. percent 2,4-dimethyl-3-pentanol/0.09 wt. percent n-propyl alcohol/0.18 wt. percent silicon tetrachloride.

Component B contained 88.63 wt. percent dicyclopentadiene/7.19 wt. percent cyclopentadiene trimer 3.52 wt. percent butadiene elastomer/0.66 wt. percent polyoxometalate catalyst.

The A and B components were reactivity tested using two pistons and a static mixer. The A and B components were first drawn into their respective piston of the reactivity tester. The components were then heated to 40° C. inside the pistons. Next, the contents of the A and B component pistons of the reactivity tester were emptied through a static mixer into a disposable adiabatic chamber.

The temperature increase during the polymerization in the adiabatic chamber was monitored. The gel time is defined as a 4° C. temperature rise from the initial temperature of 40° C.

The ligated polyoxomolybdates of Examples 1–4 provided gel times of 4.4, 3.7, 3.4, and 2.5 minutes, respectively.

Solubility Tests

The ligated polyoxometalates of Examples 1–18 were tested for solubility in hexane, together with the organoammonium octamolybdate utilized as a control. The results are given in the following table.

TABLE 1

Solubility of Organopolyoxometalates of Examples 1–18

| Example | Molecular Formula | $R^1$ | Hexane soluble | % Mo |
|---|---|---|---|---|
| Comparative Example A | $[R^1_3NH]_4\{\beta\text{-}Mo_8O_{26}\}$ | $C_{12}H_{25}$ | <10% | 23.44 |
| 1 | $[R^1_3NH]_4\{(C_6H_5PO_3)_2Mo_5O_{15}\}$ | $C_{12}H_{25}$ | >99% | 15.36 |
| 2 | $[R^1_3NH]_4\{(C_6H_5PO_3)_2Mo_5O_{15}\}$ | $C_{12}H_{25}$ | >99% | 15.36 |
| 3 | $[R^1_3NH]_4\{(C_6H_5PO_3)_2Mo_5O_{15}\}$ | $i\text{-}C_{10}H_{21}$ | >99% | 17.03 |
| 4 | $[R^1_3NH]_4\{(C_6H_5PO_3)_2Mo_5O_{15}\}$ | $i\text{-}C_8H_{17}$ | <5% | 19.53 |
| 5 | $[R^1_3NMe]_4\{(C_6H_5PO_3)_2Mo_5O_{15}\}$ | $n\text{-}C_8H_{17}$ | <5% | 19.10 |
| 6 | $[R^1_2NH_2]_4\{(C_6H_5PO_3)_2Mo_5O_{15}\}$ | $C_{13}H_{27}$ | soluble | 18.75 |
| 7 | $[R^1_3NH]_4\{(C_6H_5PO_3)_2Mo_5O_{15}\}$ | $C_{18}H_{37}$ | >99% | 11.82 |
| 8 | $[R^1_3NH]_4\{(t\text{-}BuPO_3)_2Mo_5O_{15}\}$ | $C_{12}H_{25}$ | soluble | 15.56 |
| 9 | $[R^1_3NH]_4\{(C_6H_5PO_3)_2W_5O_{15}\}$ | $C_{12}H_{25}$ | >99% | — |
| 11 | Composition of Example 11 | $C_{12}H_{25}$ | >99% | NA |
| 12 | $[R^1_3NH]_4\{(C_6H_5OPO_3)_2Mo_5O_{15}\}$ | $C_{12}H_{25}$ | >99% | 15.28 |
| 13 | $[R^1_3NH]_4\{[(HOCH_2)_2CHOPO_3]_2Mo_5O_{15}\}$ | $C_{12}H_{25}$ | >99% | 15.25 |
| 14 | $[R^1_3NH]_4\{[(HOC(O)CH_2CH_2PO_3]_2Mo_5O_{15}\}$ | $C_{12}H_{25}$ | soluble | 15.40 |
| 15 | $[R^1_3NH]_4\{(CH_3PO_3)_2Mo_5O_{15}\}$ | $C_{12}H_{25}$ | soluble | 16.00 |
| 16 | $[R^1_3NH]_2\{(H_3NC_6H_4PO_3)_2Mo_5O_{15}\}$ | $C_{12}H_{25}$ | soluble | 15.21 |
| 17 | $[R^1_3NH]_4\{(C_4H_9PO_3)_2Mo_5O_{15}\}$ | $C_{12}H_{25}$ | soluble | 15.56 |
| 18 | Composition of Example 18 | $C_{12}H_{25}$ | soluble | NA |

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

I claim:

1. An organic soluble polyoxometalate composition comprising an onium cation component and a polyoxometalate anion component wherein said onium cation is selected from the group consisting of carbon-substituted ammonium, phosphonium, arsonium, and sulfonium groups, and said anion includes a molybdate or tungstate group that incorporates a ligand, subject to the provisos that when said onium cation is an ammonium group, the total number of carbon atoms in said ammonium group is greater than 19, and when said onium cation is a phosphonium, arsonium, or a sulfonium group, the total number of carbon atoms in said groups is greater than 15.

2. The composition of claim 1 wherein said ligand is selected from the group consisting of substituted-phosphonates, substituted-phosphinates, deprotonated hydroxycarboxylates, deprotonated hydroxydicarboxylates, deprotonated hydroxytricarboxylates, deprotonated o-dihydroxybenzene, and mixtures thereof.

3. The composition of claim 2 wherein said deprotonated hydroxycarboxylate is a deprotonated hydroxyaromatic acid wherein the deprotonated hydroxy substituent and deprotonated carboxylic substituent are located on contiguous aromatic ring carbon atoms.

4. The composition of claim 2 wherein the deprotonated hydroxycarboxylate is a deprotonated α-hydroxyacid.

5. The composition of claim 2 wherein said deprotonated hydroxydicarboxylate can be protonated on at least two of its deprotonated oxygen atoms.

6. A composition selected from compounds having the following formula

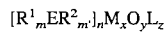

Wherein E is nitrogen, phosphorus, arsenic, or sulfur; M is molybdenum or tungsten; O is oxygen; L is a ligand selected from the group consisting of substituted-phosphonates, substituted-phosphinates, substituted arsonates, substituted stibonates, deprotonated hydroxycarboxylates, deprotonated hydroxydicarboxylates, deprotonated hydroxytricarboxylates, and mixtures thereof; when E is N, As or P (m=3 and m'=1) and when E is S (m=2 and m'=O); n=6x−2y−Qz; where x and y represent the number of M and O atoms in the anion based on the valence of +6 for molybdenum and tungsten and −2 for oxygen, and Q is the charge of the ligand L; and z is 1 to 6; $R^1$ represents a radical independently selected from the group consisting of branched and unbranched $C_1$ to $C_{20}$ alkyl, $C_2$ to $C_{20}$ alkenyl, $C_1$ to $C_{20}$ cycloalkyl, $C_6$ to $C_{24}$ aryl, $C_6$ to $C_{24}$ aryloxy, $C_7$ to $C_{40}$ alkaryl, and ring structures formed with another $R^1$ group, including those wherein one or two —$CH_2$— groups are replaced by functional groups selected from —O—, —C(O)—, —OC(O)—, and —CH(OH)—; $R^2$ is independently selected from hydrogen or $R^1$, with the proviso that when E is nitrogen the sum of all carbon atoms represented by $R^1$ and $R^2$ is at least 20, and $R^1$ and $R^2$ cannot all be hydrogen; and when E is arsenic, phosphorus, and sulfur, the sum of all carbon atoms represented by $R^1$ and $R^2$ is at least 16.

7. The composition of claim 6 wherein the substituted-phosphonate is represented by the formula

where $R^3$ is hydrogen, hydroxy, branched or unbranched $C_1$ to $C_{20}$ alkyl, branched or unbranched $C_1$ to $C_{19}$ carboxyalkyl, branched and unbranched $C_1$ to $C_{20}$ hydroxyalkyl, $C_6$ to $C_{24}$ aryl, $C_6$ to $C_{24}$ aryloxy, $C_7$ to $C_{40}$ aralkyl, deprotonated polyols, $C_6$ to $C_{24}$ protonated aminoaryl, and $C_1$ to $C_{20}$ protonated aminoalkyl.

8. The composition of claim 6 wherein the substituted-phosphinate is represented by the formula

where $R^3$ is selected from the group consisting of hydrogen, hydroxy, branched or unbranched $C_1$ to $C_{20}$ alkyl, branched or unbranched $C_1$ to $C_{19}$ carboxyalkyl, branched and unbranched $C_1$ to $C_{20}$ hydroxyalkyl, $C_6$ to $C_{24}$ aryl, $C_6$ to $C_{24}$ aryloxy, $C_7$ to $C_{40}$ aralkyl, deprotonated polyols, $C_6$ to $C_{24}$ protonated aminoaryl, and $C_1$ to $C_{20}$ protonated aminoalkyl.

9. The composition of claim 6 wherein the deprotonated hydroxycarboxylate is selected from the group consisting of $C_6$ to $C_{24}$ deprotonated hydroxyaromatic acids, and deprotonated α-hydroxyacids, wherein said deprotonated hydroxy and deprotonated carboxylic moieties on the hydroxyaromatic acid are located on contiguous aromatic ring carbon atoms.

10. The composition of claim 9 wherein the deprotonated hydroxyaromatic acids are selected from the following formulae

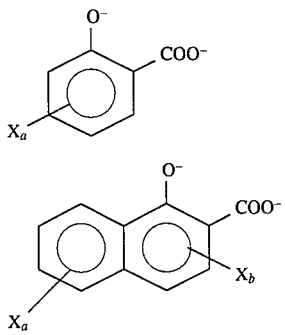

wherein X is independently selected from the group consisting of branched and unbranched $C_1$ to $C_{20}$ alkyl and halogen; a is 0 to 4, and b is 0 to 2.

11. The composition of claim 9 wherein the deprotonated α-hydroxyacids are selected from ligands of the formula

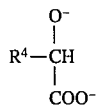

wherein $R^4$ is selected from branched and unbranched $C_1$ to $C_{20}$ alkyl.

12. The composition of claim 6 wherein the deprotonated hydroxydicarboxylates are selected from ligands of the formula

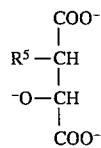

wherein $R^5$ is hydrogen, branched or unbranched $C_1$ to $C_{20}$ alkyl or $C_2$ to $C_{20}$ alkenyl.

13. The composition of claim 12 wherein one or two of the deprotonated oxygen atoms are protonated.

14. The composition of claim 6 wherein the deprotonated hydroxytricarboxylates are selected from ligands of the following formula

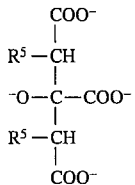

wherein $R^5$ is independently selected from the group consisting of hydrogen, branched or unbranched $C_1$ to $C_{20}$ alkyl, $C_2$ to $C_{20}$ alkenyl, and $C_6$ to $C_{24}$ aryl; and optionally one or two of the oxygen atoms in the formula above is protonated.

15. The composition of claim 6 wherein the deprotonated o-dihydroxybenzene is selected from ligands of the formula

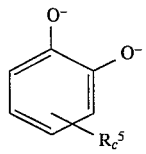

wherein $R^5$ is independently selected from the group consisting of hydrogen, branched or unbranched $C_1$ to $C_{20}$ alkyl, $C_2$ to $C_{20}$ alkenyl, and $C_6$ to $C_{24}$ aryl; and c is 0 to 4; and optionally one or two of the oxygen atoms in the formula above is protonated.

16. The composition of claim 6 wherein in said formula n is 2 to 6; x is 1 to 12; and y is 2 to 46.

17. The composition of claim 16 wherein E is nitrogen, $R^1$ is independently selected from branched or unbranched $C_8$ to $C_{18}$ alkyl; $R^2$ is selected from hydrogen, or branched or unbranched $C_1$ to $C_{18}$ alkyl; M is molybdenum; and L is a substituted-phosphonate.

18. The composition of claim 17 represented by the formula $$[R^1{}_3NR^2]_4Mo_5O_{15}(R^3PO_3)_2$$

wherein $R^3$ represents hydrogen, hydroxy, branched or unbranched $C_1$ to $C_{20}$ alkyl, branched or unbranched $C_1$ to $C_{19}$ carboxyalkyl, branched or unbranched $C_1$ to $C_{20}$ hydroxyalkyl, $C_6$ to $C_{24}$ aryl, $C_6$ to $C_{24}$ aryloxy, $C_7$ to $C_{40}$ aralkyl, deprotonated polyols, $C_6$ to $C_{24}$ protonated aminoaryl, and $C_1$ to $C_{20}$ protonated aminoalkyl.

19. The composition of claim 18 wherein $R^2$ is hydrogen.

20. The composition of claim 18 wherein $R^1$ is $C_{12}$ alkyl and $R^3$ is phenyl.

* * * * *

UNITED STATES PATENT AND TRADEMARK OFFICE
CERTIFICATE OF CORRECTION

PATENT NO. : 5,585,510

DATED : December 17, 1996

INVENTOR(S) : Anthony M. Mazany

Page 1 of 2

It is certified that error appears in the above-indentified patent and that said Letters Patent is hereby corrected as shown below:

In column 6, line 11, the term "$C^1$" should be changed to --$C_1$--.

In column 7, line 9, the term "C(O)O" should be changed to -- -C(O)O- --.

In column 7, line 10, the term "C(O)--" should be changed to -- -C(O)- --.

In column 7, line 33, the formula "$[R^1_m ER^{2m'}]_n M_x O_y L_z$" should be changed to --$[R^1_m ER^2_{m'}]_n M_x O_y L_z$--.

In column 8, line 33, the term "$[R^3 PO_2^{(2-)}]$" should be changed to --$[R^3 PO_3^{(2-)}]$--.

In column 17, line 16, the term "fined" should be changed to --fitted--.

In column 17, line 32, the term "fined" should be changed to --fitted--.

In column 17, line 49, the structure "$[C_{12}H_{25})_3 NH]_2\{[C_6H_4(O)(COO)]_2 Mo_2 O_5\}$" should be changed to --$[C_{12}H_{25})_3 NH]_4\{[HOC(O)CH_2CH_2P]_2 Mo_5 O_{21}\}$--.

In column 20, lines 22-23, the structure "$[(C_{13}H_{27})_2 NH_2]_4\{(C_6H_5P)_2 Mo_5 O_{21}\}$" should be changed to --$[(C_{13}H_{27})_2 NH_2]_4\{(C_6H_5P)_2 Mo_5 O_{21}\}$--.

In column 21, line 10, the term "heptamolybdate" should be changed to --molybdate--.

In column 21, line 15, the term "heptamolybdate" should be changed to --molybdate--.

In column 21, line 27, the structure "$[(C_{12}H_{25})_3 NH]_2\{[C_6H_4(O)(COO)]_2 Mo_5 O_2\}$" should be changed to --$[(C_{12}H_{25})_3 NH]_2\{[C_6H_4(O)(COO)]_2 Mo_2 O_5\}$--.

In column 23, line 8, the term "fined" should be changed to --fitted--.

In column 23, line 22, the term "fined" should be changed to --fitted--.

In column 23, line 49, the term "chopwise" should be changed to --dropwise--.

In column 24, line 59, the structure "$NH_4)_2 Mo_2 O_7$" should be changed to --$(NH_4)_2 Mo_2 O_7$--.

In column 25, line 58, the term "fired" should be changed to --fitted--.

In column 26, line 27, the term "fired" should be changed to --fitted--.

UNITED STATES PATENT AND TRADEMARK OFFICE
CERTIFICATE OF CORRECTION

PATENT NO. : 5,585,510

DATED : December 17, 1996

INVENTOR(S) : Anthony M. Mazany

It is certified that error appears in the above-indentified patent and that said Letters Patent is hereby corrected as shown below:

In column 28, lines 33-34, the term "$C_1$ to $C_{20}$ cycloalkyl," should be changed to --$C_5$ to $C_{20}$ cycloalkyl,--.

Signed and Sealed this

Tenth Day of June, 1997

Attest:

BRUCE LEHMAN

Attesting Officer

Commissioner of Patents and Trademarks